United States Patent [19]

Nelson

[11] 4,357,347
[45] Nov. 2, 1982

[54] PESTICIDAL PHENYLCARBAMOYLBENZIMIDATES

[75] Inventor: Stephen J. Nelson, Kalamazoo, Mich.

[73] Assignee: The Upjohn Company, Kalamazoo, Mich.

[21] Appl. No.: 326,895

[22] Filed: Dec. 4, 1981

Related U.S. Application Data

[63] Continuation-in-part of Ser. No. 233,009, Feb. 9, 1981, abandoned.

[51] Int. Cl.$^3$ ..................... A01N 37/28; A01N 37/34; C07C 119/00; C07C 121/78
[52] U.S. Cl. ................................ 424/298; 260/453.99; 424/304
[58] Field of Search ................... 260/453.99; 424/298, 424/304

[56] References Cited

U.S. PATENT DOCUMENTS

| 3,748,356 | 7/1973 | Wellinga et al. | 260/553 |
| 3,992,553 | 11/1976 | Sirrenberg et al. | 424/304 |
| 4,103,022 | 7/1978 | Sirrenberg et al. | 424/278 |
| 4,160,834 | 7/1979 | Miesel | 424/250 |
| 4,170,657 | 10/1979 | Rigterink | 424/322 |
| 4,200,653 | 4/1980 | Huff et al. | 424/322 |

FOREIGN PATENT DOCUMENTS 5944 12/1979 European Pat. Off.

OTHER PUBLICATIONS

R. Buyle et al., Helv. Chim. Acta., 46, 1073–1083 (1963).

Primary Examiner—Dolph H. Torrence
Attorney, Agent, or Firm—William G. Jameson

[57] ABSTRACT

Phenylcarbamoylbenzimidates of the formula

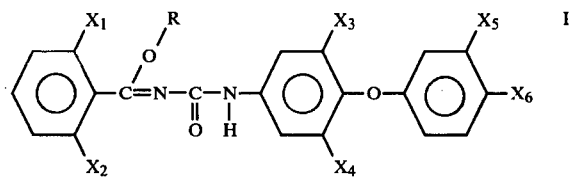

wherein $X_1$ is selected from the group consisting of methyl, trifluoromethyl, chlorine, fluorine and bromine; $X_2$ is selected from the group consisting of hydrogen, methyl, trifluoromethyl, chlorine, fluorine and bromine; R is alkyl of from 1 to 5 carbon atoms; $X_3$ and $X_4$ can be the same or different and are selected from the group consisting of hydrogen, chlorine and bromine; $X_5$ is selected from the group consisting of hydrogen, chlorine, bromine and trifluoromethyl; and $X_6$ is selected from the group consisting of cyano and nitro; with the proviso that when $X_1$ and $X_2$ are chlorine or when $X_1$ is fluorine and $X_2$ is hydrogen then R, $X_3$, $X_4$, $X_5$ and $X_6$ are respectively not 1-methylethyl, chlorine, hydrogen, chlorine and nitro; with the further proviso that when $X_1$ is fluorine and $X_2$ is hydrogen then R, $X_3$, $X_4$, $X_5$ and $X_6$ are respectively not 1-methylethyl, chlorine, hydrogen, hydrogen and nitro; and with the further proviso that when $X_1$ is florine or methyl and $X_2$ is hydrogen then R, $X_3$, $X_4$, $X_5$ and $X_6$ are respectively not ethyl, hydrogen, hydrogen, hydrogen and nitro; and with the proviso that when $X_1$ and $X_2$ are florine, then R, $X_3$, $X_4$, $X_5$ and $X_6$ are respectively not ethyl, chlorine, hydrogen, chlorine and nitro.

44 Claims, No Drawings

PESTICIDAL PHENYLCARBAMOYLBENZIMIDATES

DESCRIPTION

CROSS REFERENCE TO RELATED APPLICATIONS

This application is a continuation-in-part of copending application Ser. No. 233,009, filed Feb. 9, 1981, now abandoned.

SUMMARY OF THE INVENTION

This invention pertains to some new organic compounds and to formulations of them suitable for pesticidal use. The invention is more particularly directed to substituted phenylcarbamoylbenzimidates, and their use as insecticides and insect growth regulators.

BACKGROUND

Various phenylcarbamoylbenzimidates were prepared in conjunction with a study on the structure of carbamoylamidoximes by R. Boyle, et al., Helv. Chim. Acta, 46, 1073 (1963).

Various 2,6-difluoro-benzoylimidates, including ethyl 2,6-difluoro-N-[[[4-(2-chloro-4-trifluoromethylphenoxy)phenyl]amino]carbonyl]benzenecarboximidate, are described as insecticides especially effective against lepidopterous and coleopterous insects in European Patent Application Number 79300868.1 filed May 18, 1979 and published Dec. 12, 1979 with a Publication Number: 0 005 944. See also U.S. Pat. No. 4,200,653.

Various benzoylureas have been described in the literature and patents as insecticides including those described in U.S. Pat. Nos. 3,748,356, 4,103,022, 4,160,834, 4,170,657 and others.

U.S. Pat. No. 3,992,553 describes various benzoylureido-diphenyl ethers as insecticides, including:
4-nitro-2',6'-dichloro-4'-[N-(N'-(2-chlorobenzoyl))-ureido]-diphenyl ether,
3-chloro-4-cyano-2'-chloro-4'-[N-(N'-(2-chlorobenzoyl))-ureido]-diphenyl ether,
3-chloro-4-nitro-2'-chloro-4'-[N-(N'-(2-chlorobenzoyl))-ureido]-diphenyl ether, and
4-cyano-2',6'-dichloro-4'-[N-(N'-(2-chlorobenzoyl))-ureido]-diphenyl ether.

DETAILED DESCRIPTION OF THE INVENTION

More specifically, this invention provides compounds of Formula I, wherein $X_1$ is selected from the group consisting of methyl, trifluoromethyl, chlorine, fluorine and bromine; $X_2$ is selected from the group consisting of hydrogen, methyl, trifluoromethyl, chlorine, fluorine and bromine; R is alkyl of from 1 to 5 carbon atoms; $X_3$ and $X_4$ can be the same or different and are selected from the group consisting of hydrogen, chlorine and bromine; $X_5$ is selected from the group consisting of hydrogen, chlorine, bromine and trifluoromethyl; and $X_6$ is selected from the group consisting of cyano and nitro; with the proviso that when $X_1$ and $X_2$ are chlorine or when $X_1$ is fluorine and $X_2$ is hydrogen then R, $X_3$, $X_4$, $X_5$ and $X_6$ are respectively not 1-methylethyl, chlorine, hydrogen, chlorine and nitro; and with the further proviso that when $X_1$ is fluorine and $X_2$ is hydrogen then R, $X_3$, $X_4$, $X_5$ and $X_6$ are respectively not 1-methylethyl, chlorine, hydrogen, hydrogen and nitro; and with the further proviso that when $X_1$ is florine or methyl and $X_2$ is hydrogen then R, $X_3$, $X_4$, $X_5$ and $X_6$ are respectively not ethyl, hydrogen, hydrogen, hydrogen and nitro; and with the proviso that when $X_1$ and $X_2$ are florine, then R, $X_3$, $X_4$, $X_5$ and $X_6$ are respectively not ethyl, chlorine, hydrogen, chlorine and nitro.

In the Formula I compounds, the designation of the variable alkyl of from 1 to 5 carbon atoms means methyl, ethyl, propyl, butyl, pentyl and the isomeric forms thereof.

Compounds having the common C=N are described in European Patent Application No. 79 30068.1 as capable of existing in two different geometrically isomeric forms, depending upon the spatial disposition of the substituent groups about the C=N bond in the molecule. Following conventional chemical nomenclature, the two forms of a particular compound are designated as the E and Z isomers of the compound.

Depending upon the process chosen for preparing a particular compound, or on the way in which the condition for a particular process are varied, either of the E and Z forms may be obtained, or a mixture of the two. The isomers, having different physical properties, may be separated by physical processes known in the chemical art. It is anticipated that the isomers of a particular compound will have biological activity, but the biological effects of the isomers may not be completely identical in every case.

For the purpose of brevity throughout the subject application and claims, the formulas and chemical names referred to herein are intended to include a mixture of the E and Z forms, as well as the E and Z form substantially free of the other form.

A subgroup of Formula I compounds are those wherein $X_1$ is selected from the group consisting of methyl, chlorine, fluorine and bromine; $X_2$ is hydrogen; $X_3$, $X_4$ and $X_5$ are chlorine and $X_6$ is selected from the group consisting of cyano and nitro.

Another subgroup of compounds of Formula I are those where $X_1$ is trifluoromethyl; $X_2$ is hydrogen; R is selected from the group consisting of methyl, ethyl, propyl and isopropyl, preferably methyl and ethyl; $X_3$, $X_4$ and $X_5$ are chlorine and
$X_6$ is selected from the group consisting of cyano and nitro.

A preferred subgroup of Formula I compounds are those wherein $X_1$ is selected from the group consisting of bromine, chlorine and fluorine; $X_2$ is hydrogen; $X_3$, $X_4$ and $X_5$ are chlorine; R is selected from the group consisting of methyl, ethyl, propyl and isopropyl, preferably methyl and ethyl; and $X_6$ is nitro.

Another preferred subgroup of compounds of Formula I are those wherein $X_1$ and $X_2$ are the same and are selected from the group consisting of fluorine and chlorine; R is selected from the group consisting of methyl, ethyl, propyl, and isopropyl, preferably methyl and ethyl; $X_3$ and $X_4$ are chlorine; $X_5$ is hydrogen and $X_6$ is nitro.

Another preferred subgroup of compounds of Formula I are those wherein $X_1$ is methyl; $X_2$ and $X_5$ are hydrogen; $X_3$ and $X_4$ are chlorine; $X_6$ is nitro.

Representative compounds of this invention include the following:
Ethyl 2-chloro-N-[[[3,5-dichloro-4-(4-nitrophenoxy)phenyl]amino]carbonyl]benzenecarboximidate,
Ethyl N-[[[3,5-dichloro-4-(4-nitrophenoxy)phenyl]amino]carbonyl]-2-fluorobenzenecarboximidate,
Ethyl 2,6-dichloro-N-[[[3,5-dichloro-4-(4-nitrophenoxy)phenyl]amino]carbonyl]benzenecarboximidate, Ethyl N-[[[3,5-dichloro-4-(4-nitrophenoxy)phenyl]amino]carbonyl]-2,6-difluorobenzenecarboximidate,
Ethyl N-[[[3-chloro-4-(4-nitrophenoxy)phenyl]amino]carbonyl]-2,6-difluorobenzenecarboximidate,
Ethyl N-[[[3,5-dichloro-4-(4-nitrophenoxy)phenyl]amino]carbonyl]-2-methylbenzenecarboximidate,
Ethyl N-[[[3,5-dichloro-4-(3-chloro-4-nitrophenoxy)phenyl]amino]carbonyl]-2-fluorobenzenecarboximidate,
Ethyl 2-chloro-N-[[[3-chloro-4-(4-nitrophenoxy)phenyl]amino]carbonyl]benzenecarboximidate,
1-Methylethyl 2-chloro-N-[[[3-chloro-4-(4-nitrophenoxy)phenyl]amino]carbonyl]benzenecarboximidate,
Ethyl N-[[[3,5-dichloro-4-(3-chloro-4-nitrophenoxy)phenyl]amino]carbonyl]-2,6-difluorobenzenecarboximidate,
Ethyl 2,6-dichloro-N-[[[3,5-dichloro-4-(3-chloro-4-nitrophenoxy)phenyl]amino]carbonyl]benzenecarboximidate,
Ethyl 2-chloro-N-[[[3,5-dichloro-4-(3-chloro-4-nitrophenoxy)phenyl]amino]carbonyl]benzenecarboximidate,
Ethyl 2,6-dichloro-N-[[[3-chloro-4-(4-nitrophenoxy)phenyl]amino]carbonyl]benzenecarboximidate,
1-Methylethyl N-[[[3-chloro-4-(4-nitrophenoxy)phenyl]amino]carbonyl]-2,6-dichlorobenzenecarboximidate,
Ethyl N-[[[3-chloro-4-(4-nitrophenoxy)phenyl]amino]carbonyl]-2-fluorobenzenecarboximidate,
Ethyl 2,6-difluoro-N-[[[3,5-dichloro-4-(3-chloro-4-cyanophenoxy)phenyl]amino]carbonyl]benzenecarboximidate,
Ethyl 2,6-dichloro-N-[[[3,5-dichloro-4-(3-chloro-4-cyanophenoxy)phenyl]amino]carbonyl]benzenecarboximidate,
Ethyl 2-chloro-N-[[[3,5-dichloro-4-(3-chloro-4-cyanophenoxy)phenyl]amino]carbonyl]benzenecarboximidate,
Ethyl N-[[[3-chloro-4-(4-nitrophenoxy)phenyl]amino]carbonyl]-2-methylbenzenecarboximidate,
Ethyl 2-chloro-N-[[[3-chloro-4-(3-chloro-4-nitrophenoxy)phenyl]amino]carbonyl]benzenecarboximidate,
Ethyl N-[[[3-chloro-4-(3-chloro-4-nitrophenoxy)phenyl]amino]carbonyl]-2,6-dichlorobenzenecarboximidate,
Ethyl N-[[[3-chloro-4-(3-chloro-4-nitrophenoxy)phenyl]amino]carbonyl]-2-fluorobenzenecarboximidate,
Ethyl N-[[[3-chloro-4-(3-chloro-4-nitrophenoxy)phenyl]amino]carbonyl]-2-methylbenzenecarboximidate,
Methyl 2-chloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]2-fluorobenzenecarboximidate,
Methyl 2,6-dichloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]2,6-difluorobenzenecarboximidate,
Methyl N-[[[3-chloro-4-(4-nitrophenoxy)phenyl]amino]carbonyl]-2,6-difluorobenzenecarboximidate,
Methyl N-[[[3,5-dichloro-4-(4-nitrophenoxy)phenyl]amino]carbonyl]-2-methylbenzenecarboximidate,
Methyl N-[[[3,5-dichloro-4-(3-chloro-4-nitrophenoxy)phenyl]amino]carbonyl]-2-fluorobenzenecarboximidate,
Methyl 2-chloro-N-[[[3-chloro-4-(4-nitrophenoxy)phenyl]amino]carbonyl]benzenecarboximidate,
Methyl N-[[[3,5-dichloro-4-(3-chloro-4-nitrophenoxy)phenyl]amino]carbonyl]-2,6-difluorobenzenecarboximidate,
Methyl 2,6-dichloro-N-[[[3,5-dichloro-4-(3-chloro-4-nitrophenoxy)phenyl]amino]carbonyl]benzenecarboximidate,
Methyl 2-chloro-N-[[[3,5-dichloro-4-(3-chloro-4-nitrophenoxy)phenyl]amino]carbonyl]benzenecarboximidate,
Methyl 2,6-dichloro-N-[[[3-chloro-4-(4-nitrophenoxy)phenyl]amino]carbonyl]benzenecarboximidate,
Methyl N-[[[3-chloro-4-(4-nitrophenoxy)phenyl]amino]carbonyl]-2-fluorobenzenecarboximidate,
Methyl 2,6-difluoro-N-[[[3,5-dichloro-4-(3-chloro-4-cyanophenoxy)phenyl]amino]carbonyl]benzenecarboximidate,
Methyl 2,6-dichloro-N-[[[3,5-dichloro-4-(3-chloro-4-cyanophenoxy)phenyl]amino]carbonyl]benzenecarboximidate,
Methyl 2-chloro-N-[[[3,5-dichloro-4-(3-chloro-4-cyanophenoxy)phenyl]amino]carbonyl]benzenecarboximidate,
Methyl N-[[[3-chloro-4-(4-nitrophenoxy)phenyl]amino]carbonyl]-2-methylbenzenecarboximidate,
Methyl 2-chloro-N-[[[3-chloro-4-(3-chloro-4-nitrophenoxy)phenyl]amino]carbonyl]benzenecarboximidate,
Methyl N-[[[3-chloro-4-(3-chloro-4-nitrophenoxy)phenyl]amino]carbonyl]-2,6-dichlorobenzenecarboximidate,
Methyl N-[[[3-chloro-4-(3-chloro-4-nitrophenoxy)phenyl]amino]carbonyl]-2-fluorobenzenecarboximidate,
Methyl N-[[[3-chloro-4-(3-chloro-4-nitrophenoxy)phenyl]amino]carbonyl]-2,6-difluorobenzenecarboximidate,
Methyl N-[[[3-chloro-4-(3-chloro-4-nitrophenoxy)phenyl]amino]carbonyl]-2-methylbenzenecarboximidate,
Ethyl 2,6-dichloro-N-[[[4-(nitrophenoxy)-phenyl]amino]carbonyl]benzenecarboximidate,
1-Methylethyl 2,6-dichloro-N-[[[3,5-dichloro-4-(3-chloro-4-cyanophenoxy)phenyl]amino]carbonyl]benzenecarboximidate,
Ethyl 2-chloro-N-[[[4-(4-nitrophenoxy)phenyl]amino]carbonyl]benzenecarboximidate,
1-Methylethyl 2-chloro-N-[[[3-chloro-4-(3-chloro-4-nitrophenoxy)phenyl]amino]carbonyl]benzenecarboximidate,
Methyl 2-chloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]-2-fluorobenzenecarboximidate,
Methyl 2,6-dichloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]-2,6-difluorobenzenecarboximidate,
Methyl N-[[[3-chloro-4-(4-nitrophenoxy)phenyl]amino]carbonyl]-2,6-difluorobenzenecarboximidate,
Methyl N-[[[3,5-dichloro-4-(4-nitrophenoxy)phenyl]amino]carbonyl]-2-methylbenzenecarboximidate,
Methyl 2-chloro-N-[[[3-chloro-4-(4-nitrophenoxy)phenyl]amino]carbonyl]benzenecarboximidate,
Methyl N-[[[3-chloro-4-(4-nitrophenoxy)phenyl]amino]carbonyl]-2,6-dichlorobenzenecarboximidate, Methyl N-[[[3-chloro-4-(4-nitrophenoxy)phenyl]amino]carbonyl]-2-fluorobenzenecarboximidate, Methyl N-[[[3-chloro-4-(4-nitrophenoxy)phenyl]amino]carbonyl]-2-methylbenzenecarboximidate, 1-Methylethyl 2-chloro-N-[[[3,5-dichloro-4-(4-nitrophenoxy)phenyl]amino]carbonyl]benzenecarboximidate, 1-Methylethyl N-[[[3,5-dichloro-4-(4-nitrophenoxy)phenyl]amino]carbonyl]-2-fluorobenzenecarboximidate, 1-Methylethyl 2,6-dichloro-N-[[[3,5-dichloro-4-(4-nitrophenoxy)phenyl]amino]carbonyl]benzenecarboximidate, 1-Methylethyl N-[[[3,5-dichloro-4-(4-nitrophenoxy)phenyl]amino]carbonyl]-2,6-difluorobenzenecarboximidate, 1-Methylethyl N-[[[3-chloro-4-(4-nitrophenoxy)phenyl]amino]carbonyl]-2,6-difluorobenzenecarboximidate, 1-Methylethyl N-[[[3,5-dichloro-4-(4-nitrophenoxy)phenyl]amino]carbonyl]-2-methylbenzenecarboximidate, 1-Methylethyl N-[[[3-chloro-4-(4-nitrophenoxy)phenyl]amino]carbonyl]-2-fluorobenzenecarboximidate, 1-Methylethyl N-[[[3-chloro-4-(4-nitrophenoxy)phenyl]amino]carbonyl]-2-methylbenzenecarboximidate.

These formula I compounds can be prepared by reacting the appropriate benzimidic ester of Formula II with an isocyanate of Formula III in a suitable inert solvent at temperatures ranging from 0° to 100° C., preferably 15° to 50° C. A catalytic amount of a tertiary organic base, such as triethylamine may be added. Alternatively, the benzimidates may be reacted as their addition salts, for example, hydrochloride, fluorosulfonate, or fluoroborate salts, in the presence of a 0 to 10% excess of a tertiary organic base such as triethylamine. Illustrative of suitable inert solvents for the reaction are toluene, methylene chloride, tetrahydrofuran, acetone, and ethyl acetate. Acetone is a particularly effective solvent.

When the reaction has proceeded to substantial completion, the product (I) can be recovered from the reaction by known procedures. For example crystallization and/or chromatography.

Alternatively, the benzimidic ester of Formula II can be reacted sequentially with phosgene and an appropriate aniline to give the compounds of this invention. The reaction of the benzimidic ester with phosgene can be carried out in a suitably inert solvent such as benzene, toluene, methylene chloride, or ethyl acetate in the presence of an acid scavenger such as triethylamine and at temperatures ranging from −20° C. to 50° C. The resultant chlorocarbonyl benzimidate intermediate can then be reacted with an appropriate aniline in the presence of an acid scavenger such as triethylamine to yield the title compounds.

The benzimidic esters of Formula II can be prepared from the corresponding benzamide by reaction with appropriate alkylating agents such as trialkyloxonium salts or alkyl esters of fluorosulfuric acid. The reaction of a benzamide with the alkylating agent can be conducted in a suitably inert solvent such as methylene chloride, toluene and ethylene dichloride at temperatures ranging from 0° C. to 80° C. The benzimidic ester is recovered from the reaction mixture by extraction with aqueous hydrochloric acid. The acidic extract is made alkaline with a suitable base such as sodium hydroxide and extracted with an organic solvent such as benzene, methylene chloride and the like.

Alternatively, the benzimidate ester addition salts, for example tetrafluoroborate or fluorosulfonate salts, may be obtained directly from the reaction mixture by filtration, and used directly in the next step.

A procedure for the preparation of isopropyl fluorosulfonate and its subsequent reaction with benzamides is given in the following Example 3. The preparation of isopropyl fluorosulfonate is essentially that given by G. A. Olah, J. Nishimuna, and Y. K. Mo in Synthesis, 1973, 661.

Phenoxyanilines of Formula IV can be prepared by procedures given in U.S. Pat. No. 3,992,553.

Isocyanates can be prepared by the action of phosgene on the anilines. For example, see Shriner, Horne and Cox, Organic Synthesis, Collective Volume II, 453 (1943).

The Formula I compounds can also be prepared by reacting a 1,3,5-oxadiazinedione derivative (V) with the appropriate alcohol according to procedures described in European Patent Application Number 79300068.1 filed May 5, 1979 and referred to in the Background of the subject application.

The 1,3,5-oxadiazinedione derivatives (V) can be prepared as described in German Offenlegungsschrift No. 2732115 and U.S. Pat. No. 4,150,158.

The following are detailed examples which show the preparation of various compounds described in this invention. They are to be construed as illustrations of said compounds and not as limitations thereof. Those skilled in the art will promptly recognize appropriate variations from the procedures both as to reactants as well as reaction conditions and techniques.

EXAMPLE 1

Preparation of the compound ethyl 2-chloro-N-[[[3,5-dichloro-4-(4-nitrophenoxy)phenyl]amino]carbonyl]benzenecarboximidate.

A mixture of ethyl 2-chlorobenzimidate hydrofluoroborate (1.90 g., 7.00 mmol), 3,5-dichloro-4-(4-nitrophenoxy)phenylisocyanate (2.28 g., 7.00 mmol) and triethylamine (0.72 g., 7.20 mmol) in acetone (20 ml) is stirred at room temperature for four hours under an atmosphere of dry nitrogen. The reaction mixture is concentrated under reduced pressure and the residue partitioned between ethyl acetate and water. The organic phase is washed sequentially with dilute hydrochloric acid, dilute sodium bicarbonate, and brine. After drying over sodium sulfate, the ethyl acetate solution is concentrated under reduced pressure and the residue chromatographed over silica gel eluting with 20% ethyl acetate in hexane. The product fractions are combined and concentrated under reduced pressure to leave the title compound as an amorphous solid.

A sample of the title compound was prepared by a procedure essentially the same as described above and gave a product having an nmr spectrum consistent with the desired product.

Analysis Calc'd for: $C_{22}H_{16}Cl_3N_3O_5$ C, 51.94; H, 3.17; N, 8.26; Cl, 20.91. Found: c, 52.05; H, 3.08; N, 8.29; Cl, 20.87.

Mass spectrum: Calc'd: 508.745. Found: 507 and 509.

EXAMPLE 2

Starting with the appropriate benzimidic ester addition salt and the appropriate isocyanate, the following compounds are prepared by procedures similar to Example 1.

Ethyl N-[[[3,5-dichloro-4-(4-nitrophenoxy)phenyl]amino]carbonyl]-2-fluorobenzenecarboximidate, Analysis Calc'd for: $C_{22}H_{16}Cl_2FN_3O_5$ C, 53.68; H, 3.28; N, 8.54; Cl, 14.40. Found: C, 53.54; H, 3.62; N, 8.64; Cl, 14.17.

Ethyl 2,6-dichloro-N-[[[3,5-dichloro-4-(4-nitrophenoxy)phenyl]amino]carbonyl]benzenecarboximidate, Analysis Calc'd for: $C_{22}H_{15}Cl_4N_3O_5$ C, 48.64; H, 2.78; N, 7.74; Cl, 26.11. Found: C, 48.61; H, 2.98; N, 7.78; Cl, 26.20.

Ethyl N-[[[3,5-dichloro-4-(4-nitrophenoxy)phenyl]amino]carbonyl]-2,6-difluorobenzenecarboximidate, Analysis Calc'd for: $C_{22}H_{15}Cl_2F_2N_3O_5$ C, 51.78; H, 2.96; N, 8.23; Cl, 13.90. Found: C, 52.03; H, 3.36; N, 8.07; Cl, 14.02.

Mass spectrum Calc'd: 510.280. Found: 509, 511, and 513.

Ethyl N-[[[3-chloro-4-(4-nitrophenoxy)phenyl]amino]carbonyl]-2,6-difluorobenzenecarboximidate, Analysis Calc'd for: $C_{22}H_{16}ClF_2N_3O_5$ C, 55.53; H, 3.39; N, 8.83; Cl, 7.45. Found: C, 55.82; H, 3.31; N, 8.74; Cl, 7.25.

Mass spectrum Calc'd: 475.835. Found: 475, 477.

Ethyl N-[[[3,5-dichloro-4-(4-nitrophenoxy)phenyl]amino]carbonyl]-2-methylbenzenecarboximidate, Analysis Calc'd for: $C_{23}H_{19}Cl_2N_3O_5$ C, 56.57; H, 3.92; N, 8.61; Cl, 14.52. Found: C, 56.34; H, 4.05; N, 8.70; Cl, 14.44.

Ethyl N-[[[3,5-dichloro-4-(3-chloro-4-nitrophenoxy)phenyl]amino]carbonyl]-2-fluorobenzenecarboximidate, Analysis Calc'd for: $C_{22}H_{15}Cl_3FN_3O_5$ C, 50.17; H, 2.87; N, 7.98; Cl, 20.19. Found: C, 49.76; H, 2.99; N, 7.60; Cl, 19.91.

Ethyl 2-chloro-N-[[[3-chloro-4-(4-nitrophenoxy)phenyl]amino]carbonyl]benzenecarboximidate, Analysis Calc'd for: $C_{22}H_{17}Cl_2N_3O_5$ C, 55.71; H, 3.61; N, 8.86; Cl, 14.95. Found: C, 55.69; H, 3.77; N, 9.01; Cl, 15.10.

1-Methylethyl 2-chloro-N-[[[3-chloro-4-(4-nitrophenoxy)phenyl]amino]carbonyl]benzenecarboximidate, Analysis Calc'd for: $C_{23}H_{19}Cl_2N_3O_5$ C, 56.57; H, 3.92; N, 8.61; Cl, 14.52. Found: C, 56.46; H, 4.08; N, 8.55; Cl, 14.58.

Ethyl N-[[[3,5-dichloro-4-(3-chloro-4-nitrophenoxy)phenyl]amino]carbonyl]-2,6-difluorobenzenecarboximidate, Analysis Calc'd for: $C_{22}H_{14}Cl_3F_2N_3O_5$ C, 48.51; H, 2.59; N, 7.71; Cl, 19.53. Found: C, 48.62; H, 2.79; N, 7.81; Cl. 19.50.

Ethyl 2,6-dichloro-N-[[[3,5-dichloro-4-(3-chloro-4-nitrophenoxy)phenyl]amino]carbonyl]benzenecarboximidate, Analysis Calc'd for: $C_{22}H_{14}Cl_5N_3O_5$ C, 45.75; H, 2.44; N, 7.27; Cl, 30.69. Found: C, 45.89; N, 2.67; N, 7.34; Cl, 30.17.

Ethyl 2-chloro-N-[[[3,5-dichloro-4-(3-chloro-4-nitrophenoxy)phenyl]amino]carbonyl]benzenecarboximidate, Analysis Calc'd for: $C_{22}H_{15}Cl_4N_3O_5$ C, 48.65; H, 2.78; N, 7.74; Cl, 26.11. Found: C, 48.86; H, 3.05; N, 7.76; Cl, 26.35.

Ethyl 2,6-dichloro-N-[[[3-chloro-4-(4-nitrophenoxy)phenyl]amino]carbonyl]benzenecarboximidate, Analysis Calc'd for: $C_{22}H_{16}Cl_3N_3O_5$ C, 51.94; H, 3.17; N, 8.26; Cl, 20.96. Found: C, 51.85; H, 3.19; N, 8.40; Cl, 20.96.

Mass spectrum Calc'd: 508.745. Found: 507, 509, 511.

1-Methylethyl N-[[[3-chloro-4-(4-nitrophenoxy)phenyl]amino]carbonyl]-3,6-dichlorobenzenecarboximidate, Analysis Calc'd for: $C_{22}H_{18}Cl_3N_3O_5$ C, 52.84; H, 3.47; N, 8.04; Cl, 20.35. Found: C, 52.61; H, 3.59; N, 7.99; Cl, 20.02.

Mass spectrum Calc'd: 522.772. Found: 521, 523.

Ethyl N-[[[3-chloro-4-(4-nitrophenoxy)phenyl]amino]carbonyl]-2-fluorobenzenecarboximidate, Analysis Calc'd for: $C_{22}H_{17}ClFN_3O_5$ C, 57.71; H, 3.74; N, 9.18; Cl, 7.74. Found: C, 57.60; H, 3.77; N, 9.34; Cl, 8.22.

Mass spectrum Calc'd: 457.845. Found: 457, 459.

Ethyl 2,6-Difluoro-N-[[[3,5-dichloro-4-(3-chloro-4-cyanophenoxy)phenyl]amino]carbonyl]benzenecarboximidate, Analysis Calc'd for: $C_{23}H_{14}Cl_3F_2N_3O_3$ C, 52.65; H, 2.69; N, 8.01; Cl, 20.27. Found: C, 52.58; H, 2.76; N, 8.06; Cl, 20.30.

Mass spectrum Calc'd: 524.738. Found: 523, 525, 527.

Ethyl 2,6-dichloro-N-[[[3,5-dichloro-4-(3-chloro-4-cyanophenoxy)phenyl]amino]carbonyl]benzenecarboximidate, Analysis Calc'd for: $C_{23}H_{14}Cl_5N_3O_3$ C, 49.54; H, 2.53; N, 7.54; Cl, 31.79. Found: C, 49.58; H, 2.62; N, 7.49; Cl, 31.71.

Mass spectrum Calc'd: 557.648. Found: 555, 557, 559, 561.

Ethyl 2-chloro-N-[[[3,5-dichloro-4-(3-chloro-4-cyanophenoxy)phenyl]amino]carbonyl]benzenecarboximidate, Analysis Calc'd for: $C_{23}H_{15}Cl_4N_3O_3$ C, 52.80; H, 2.89; N, 8.03; Cl, 27.10. Found: C, 52.77; H, 3.12; N, 8.17; Cl, 26.63.

Ethyl N-[[[3-chloro-4-(4-nitrophenoxy)phenyl]amino]carbonyl]-2-methylbenzenecarboximidate, Analysis Calc'd for: $C_{23}H_{20}ClN_3O_5$ C, 60.86; H, 4.44; N, 9.26; Cl, 7.81. Found: C, 60.92; H, 4.56; N, 8.86; Cl, 7.80.

Mass spectrum Calc'd: 522.772. Found: 521, 523.

Ethyl 2-chloro-N-[[[3-chloro-4-(3-chloro-4-nitrophenoxy)phenyl]amino]carbonyl]benzenecarboximidate, Analysis Calc'd for: $C_{22}H_{16}Cl_3N_3O_5$ C, 51.94; H, 3.17; N, 8.26; Cl, 20.91. Found: C, 51.88; H, 3.37; N, 8.34; Cl, 20.61.

Mass spectrum Calc'd: 508.745. Found: 507, 509.

Ethyl N-[[[3-chloro-4-(3-chloro-4-nitrophenoxy)phenyl]amino]carbonyl]-2,6-dichlorobenzenecarboximidate, Analysis Calc'd for: $C_{22}H_{15}Cl_4N_3O_5$ C, 48.65; H, 2.78; N, 7.74; Cl, 26.11. Found: C, 48.65; H, 2.90; N, 7.65; Cl, 25.75.

Mass spectrum Calc'd: 543.190. Found: 541, 543, 545.

Ethyl N-[[[3-chloro-4-(3-chloro-4-nitrophenoxy)phenyl]amino]carbonyl]-2-fluorobenzenecarboximidate, Analysis Calc'd for: $C_{22}H_{16}Cl_2FN_3O_5$ C, 53.68; H, 3.28; N, 8.54; Cl, 14.40. Found: C, 53.35; H, 3.28; N, 8.50; Cl, 14.40.

Mass spectrum Calc'd: 492.290. Found: 491, 493.

Ethyl N-[[[3-chloro-4-(3-chloro-4-nitrophenoxy)phenyl]amino]carbonyl]-2-methylbenzenecarboximidate, Analysis Calc'd for: $C_{23}H_{19}Cl_2N_3O_5$ C, 56.57; H, 3.92; N, 8.61; Cl, 14.52. Found: C, 56.44; H, 4.09; N, 8.34; Cl, 14.00.

Mass spectrum Calc'd: 488.327. Found: 487

Ethyl 2,6-dichloro-N-[[[4-(nitrophenoxy)-phenyl]amino]carbonyl]benzenecarboximidate, Analysis Calc'd for: $C_{22}H_{17}Cl_2N_3O_5$: C, 55.71; H, 3.61; N, 8.86; Cl, 14.95. Found: C, 55.74; H, 3.61; N, 9.28; Cl, 15.01.

1-Methylethyl 2-chloro-N-[[[3-chloro-4-(3-chloro-4-nitrophenoxy)phenyl]amino]carbonyl]benzenecarboximidate, Analysis Calc'd for: $C_{23}H_{18}Cl_3N_3O_5$: C, 52.84; H, 3.47; N, 8.04; Cl, 20.35. Found: C, 52.67; H, 3.55; N, 8.16; Cl, 20.25.

1-Methylethyl 2,6-dichloro-N-[[[3,5-dichloro-4-(3-chloro-4-cyanophenoxy)phenyl]amino]carbonyl]benzenecarboximidate, Analysis Calc'd for: $C_{24}H_{16}Cl_5N_3O_3$: C, 50.42; H, 2.82; N, 7.35; Cl, 31.01. Found: C, 50.54; H, 2.84; N, 7.32; Cl, 31.05.

EXAMPLE 3

Preparation of 1-Methylethyl 2-chlorobenzene carboximidate

Ten grams (0.100 moles) of fluorosulfuric acid is placed in a flask equipped with a dry-ice condenser and maintained at $-78°$ (dry ice/isopropanol bath) under an atmosphere of dry nitrogen. To this is added about 25 ml of propylene with moderate stirring giving an orange-colored solution. The reaction mixture is stirred for 15 min. and then diluted with 100 ml of methylene chloride, precooled to $-50°$ C. To this is added at once 15.6 g (0.100 moles) of 2-chlorobenzamide and the mixture stirred at ambient temperature for 18 hrs. giving a deep purple-red solution. The reaction mixture is then poured into 300 ml. of 1 N sodium hydroxide with rapid stirring. After standing briefly the layers are separated. Dilution with saturated sodium chloride solution and methylene chloride facilitates separation of the layers. The turbid organic phase is dried ($Na_2SO_4$), filtered through celite filter aid, and the solvent removed in vacuo. The residue is triturated with hexane (Skellysolve B ®) and filtered, thereby removing any unreacted 2-chlorobenzamide. The filtrate is distilled under reduced pressure to afford 1-methylethyl 2-chlorobenzenecarboximidate as an oil.

The compounds of Formula I can be used to control infestations of invertebrate pests, such as insects and ticks, particularly mature and/or immature forms of insects in agriculture, industry, and around the home.

Efficacy against one or more species of insect pests has been demonstrated by selected compounds of the present invention, in mortality tests, at concentrations as low as 0.4 ppm, depending upon the specific pest and specific compound utilized. Some invertebrate animal pests will be more sensitive to given compounds than others, and others might be quite resistant.

Particularly insecticidally active compounds of Formula I against southern armyworm larvae (*Spodoptera eridania*), cabbage looper larvae (*Trichoplusia ni*), tobacco budworm (*Heliothis virescens*), or yellow-fever mosquito larvae (*Aedes aeqypti*) include:

Ethyl 2-chloro-N-[[[3,5-dichloro-4-(4-nitrophenoxy)-phenyl]amino]carbonyl]benzenecarboximidate, Ethyl N-[[[3,5-dichloro-4-(4-nitrophenoxy)phenyl]amino]carbonyl]-2-fluorobenzenecarboximidate, Ethyl 2,6-dichloro-N-[[[3,5-dichloro-4-(4-nitrophenoxy)phenyl]amino]carbonyl]benzenecarboximidate, Ethyl N-[[[3,5-dichloro-4-(4-nitrophenoxy)phenyl]amino]carbonyl]-2,6-difluorobenzenecarboximidate, Ethyl N-[[[3-chloro-4-(4-nitrophenoxy)phenyl]amino]carbonyl]-2,6-difluorobenzenecarboximidate, Ethyl N-[[[3,5-dichloro-4-(4-nitrophenoxy)phenyl]amino]carbonyl]-2-methylbenzenecarboximidate, Ethyl 2-chloro-N-[[[3-chloro-4-(4-nitrophenoxy)phenyl]amino]carbonyl]benzenecarboximidate, Ethyl 2,6-dichloro-N-[[[3-chloro-4-(4-nitrophenoxy)phenyl]amino]carbonyl]benzenecarboximidate, Ethyl N-[[[3-chloro-4-(4-nitrophenoxy)phenyl]amino]carbonyl]-2-fluorobenzenecarboximidate, Ethyl N-[[[3,5-dichloro-4-(3-chloro-4-nitrophenoxy)phenyl]amino]carbonyl]-2-fluorobenzenecarboximidate, 1-Methylethyl 2-chloro-N-[[[3-chloro-4-(4-nitrophenoxy)phenyl]amino]carbonyl]benzenecarboximidate, Ethyl N-[[[3,5-dichloro-4-(3-chloro-4-nitrophenoxy)phenyl]amino]carbonyl]-2,6-difluorobenzenecarboximidate, Ethyl 2,6-dichloro-N-[[[3,5-dichloro-4-(3-chloro-4-nitrophenoxy)phenyl]amino]carbonyl]benzenecarboximidate, Ethyl 2-chloro-N-[[[3,5-dichloro-4-(3-chloro-4-nitrophenoxy)phenyl]amino]carbonyl]benzenecarboximidate, 1-Methylethyl N-[[[3-chloro-4-(4-nitrophenoxy)phenyl]amino]carbonyl]-2,6-dichlorobenzenecarboximidate, especially the first nine-mentioned compounds.

The compounds of this invention can be utilized for control of insect pests in the form of the pure compounds as prepared in the Examples, as technical grade compounds from commercial productions, or as mixtures of the specific compounds. On the other hand, practical considerations indicate the desirability of providing those skilled in the pesticide art with formulations comprising a diluent carrier with or without adjuvants that will promote the distribution of the active compounds where pest control is desired and thus enhance efficacy and economics.

There are many different kinds of diluent carriers suitable for the method and formulation embodiments of this invention. Dispersible carriers are commonly used in the art. Such carriers may or may not include adjuvants such as wetting agents, emulsifying agents, stickers, and other components that indirectly promote efficacy.

The new compounds of Formula I are useful against insects in formulations, e.g., as dusts, wettable powders, emulsifiable concentrates, aqueous dispersions, solutions, and flowable creams for applications to a situs, soil, plants, and foliage, seeds, or other parts of plants. Granular formulations can be prepared and applied to soil or on surfaces. Moreover, the new compounds of Formula (I) of this invention can be the sole active agent in a formulation or other insecticidal, or nematocidal components may be included.

The new solid compounds of Formula (I) can be readily formulated as dusts by grinding a mixture of the compound and a pulverulent carrier in the presence of each other. Grinding is conveniently accomplished in a ball mill, a hammermill, or by air-blast micronization. A suitable ultimate particle size is less than 60 microns. Preferably, 95% of the particles are less than 50 microns, and about 75% are 3 to 7 microns. Dusts of that degree of comminution are conveniently free-flowing and can be applied to animals, inanimate matter, fruit trees, crop plants, and soil so as to effect thorough distribution and coverage. Dusts are particularly adapted for effectively controlling insects and mites over wide areas when applied by airplane. They are also indicated for application to the undersides of plant foilage.

Representative suitable pulverulent carriers include the natural clays such as China, Georgia, Barden, Attapulgus, Kaolin, and Bentonite clays; minerals in their natural forms as they are obtained from the earth such as talc, pyrophillite, quartz, diatomaceous earth, Fuller's earth, chalk, sulfur, silica and silicates; chemically modified minerals such as washed bentonite and colloidal silica; and organic flours such as wood, walnut shell, soybean, cottonseed, and tobacco flours, and free-flowing, hydrophobic starches.

Dusts can also be prepared by dissolving the compounds of Formula I in a volatile solvent such as methylene chloride, mixing the solution with a pulverulent carrier and evaporating the solvent.

The proportions of pulverulent carrier and active compound (Formula I) can vary over a wide range depending upon the use of it, pests to be controlled, and the conditions of treatment. In general, dust formulations can contain up to about 90% (on a weight basis) of the active ingredient.

The dispersible powder formulations of this invention are prepared by incorporating a surfactant in a dust formulation prepared as described above. When about 0.1% to about 12% of a surfactant is incorporated in a dust, the dispersible powder thus obtained is particularly adapted for further admixture with water for spraying on inanimate matter and products, fruit trees, field crops, soil, and livestock. The dispersible powders can be admixed with water to obtain any desired concentration of active ingredient, and the mixture can be applied in amounts sufficient to obtain predetermined rates of application and uniform distribution. With this flexibility in mind, the dispersible powders of the invention can conveniently comprise preferably about 5% to about 80% of active ingredient.

Representative surfactants useful for preparing dispersible powder formulations of this invention include alkyl sulfates and sulfonates, alkyl aryl sulfonates, sulfosuccinate esters, polyoxyethylene sulfates, polyoxyethylene sorbitan monolaurate, alkyl aryl polyether sulfates, alkyl aryl polyether alcohols, alkyl naphthalene sulfonates, alkyl quaternary ammonium salts, sulfated fatty acids, and esters, sulfated fatty acid amides, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyethoxy ethanols (Tritons X-151, X-161, X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul N$_2$S). It will be understood, of course, that the sulfate and sulfonate surfactants suggested above will preferably be used in the form of their soluble salts, for examples, their sodium salts. All of these surfactants are capable of reducing the surface tension of water in concentrations of about 1% or less. The dispersible powder formulations can be prepared with a mixture of surfactants of the types indicated if desired.

A suitable dispersible powder formulation is obtained by blending and milling 327 lbs. of Georgia Clay, 4.5 lbs. of isooctylphenoxy polyethoxy ethanol (Triton X-100) as a wetting agent, 9 lbs. of a polymerized sodium salt of substituted benzoid long-chain sulfonic acid (Daxad 27) as a dispersing agent, and 113 lbs. of the active ingredient, e.g., the compound embodiment of Example 1 or any of the compounds of Example 2. The resulting formulation has the following percentage compositions (parts herein are by weight unless otherwise specified).

| Active Ingredient | 25% |
|---|---|
| Isooctylphenoxy Polyethoxy Ethanol | 1% |
| Polymerized sodium salt of substituted benzoid long-chain sulfonic acid | 2% |
| Georgia Clay | 72% |

This formulation, when dispersed in water at the rate of about 1 lb. per 100 gals., gives a spray formulation containing about 0.12% (1200 ppm) active ingredient which can be applied against insects, on plants, fruit trees, or other habitats.

If desired, dispersants such as methylcellulose, polyvinyl alcohol, sodium ligninsulfonates, and the like can be included in the dispersible powder formulations of this invention. Adhesive or sticking agents such as vegetable oils, naturally occuring gums, casein, Zonarez B, a series of polymerized terpenes, Unirez 709, a maleic acid-derived resin, Polypale, partially dimerized resin acids, and Dymerex, a dimeric resin acid, and others can also be included. Corrosion inhibitors such as epichlorohydrin and anti-foaming agents such as stearic acid can also be included. Methods for including these agents in pesticidal formulation are well-known in the art and are applicable to this invention.

The compounds of Formula I of this invention can also be applied to insects, objects, or situs in aqueous sprays without a solid carrier. Since, however, the compounds themselves are relatively insoluble in water, they are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used, the solvent carrier will dissolve in the water and any excess of compounds of Formula I will be thrown out of the solution. In an oil-in-water emulsion, the solvent phase is dispersed in the water phase and the dispersed phase contains the active ingredient. In this way, uniform distribution of a water insoluble active ingredient is achieved in an aqueous spray. A solvent carrier in which the new compounds of Formula I are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentrations useful for applying to insects and mites.

The emulsifiable concentrates of the invention are prepared, therefore, by dissolving the active ingredient and a surfactant in a substantially water-immiscible solvent carrier (i.e., a solvent carrier which is soluble in water to the extent of less than 2.5% by volume at temperatures on the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with a solvent carrier in order to enhance the solubility of the active ingredient. Aqueous emulsions are then prepared by mixing with water to given any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5% to about 50% by weight, preferably from about 10% to about 40%. A concentrate comprising 20% (by weight) of the compound dissolved in a water-immiscible solvent of the kind noted above can be admixed with an aqueous medium in the proportions of 13 ml. of concentrate with 1 gallon of medium to give a mixture containing 700 parts of active ingredient per million parts of liquid carrier. Similarly, 1 quart of a 20% concentrate mixed with 40 gallons of water provides about 1200 ppm (parts per million) of active ingredient. In the same manner, more concentrated solutions of active ingredient can be prepared.

The concentrate formulations of the invention which are intended for use in the form of aqueous dispersions of emulsions can also comprise a humectant, that is to say, an agent which will delay the drying of the composition in contact with material to which it has been applied. Suitable humectants include glycerol, diethylene glycol, solubilized lignins, such as calcium ligninsulfonate, and the like.

The granular formulations of this invention are convenient for application to soil when persistence is desired. Granulars are readily applied broadcast or by localized, e.g., in-the-row applications. The individual granules may be any desired size from 10 to 60 mesh, advantageously 20 to 40 mesh. Granulars are prepared by dissolving the active compound in a solvent such as methylene chloride, xylene, or acetone and applying the solution to a quantity of a granulated absorbent carrier. Representative granulated absorbent carriers include ground corn cobs, ground walnut shells, ground peanut hulls, and the like. If desired, the impregnated granulated absorbent carrier can be coated with a coating that will preserve the integrity of the granular until it is applied to an object or situs favorable for release of the active ingredient.

The rates of application to insects, soil, or other situs will depend upon the species of the pest organism to be controlled, the presence or absence of desirable living organisms, temperature conditions of treatment, and the method and efficiency of application. In general, insecticidal activity is obtained when the compounds are applied at concentrations of about 5 to about 2000 ppm, preferably at concentrations of about 30 to about 1000 ppm and preferably at a rate of from about 0.05 to 5 lbs/acre, more preferably 0.1 to 1 lb/acre.

In addition to insecticidal activity the compounds of Formula I are contemplated to exhibit activity against other invertebrate pests, including arachnoid pests such as ticks when applied at concentrations of about 0.1 to about 5% as a dip.

The formulations containing compounds of Formula I according to the invention, can be applied to insects, soil or other situs by conventional methods. For example, an area of soil, a building, or plants can be treated by applying a wettable powder from a hand-operated knapsack sprayer. Dips can be used for livestock. Dusts can be applied by power dusters, or by hand-operated dusters. Creams and ointment formulations can be applied to skin or objects for prolonged protection from insects or mites.

The active compounds of the invention can also be formulated in relatively dilute proportions in a dispersible insecticide carrier for household applications. Thus, the active compounds can be formulated in dusts having from about 0.1% to 5.0% active ingredient with deodorized kerosene for aerosol applications.

It will, of course, be appreciated that the conditions encountered when applying the method and formulations of this invention to actual practice can vary widely. Included among the variables that may be encountered are the degree of infestation by pests, the particular pest to be controlled, the particular situs being treated, the type of plants, the prevailing weather conditions, such as temperature, relative humidity, rainfall, dews, and so forth.

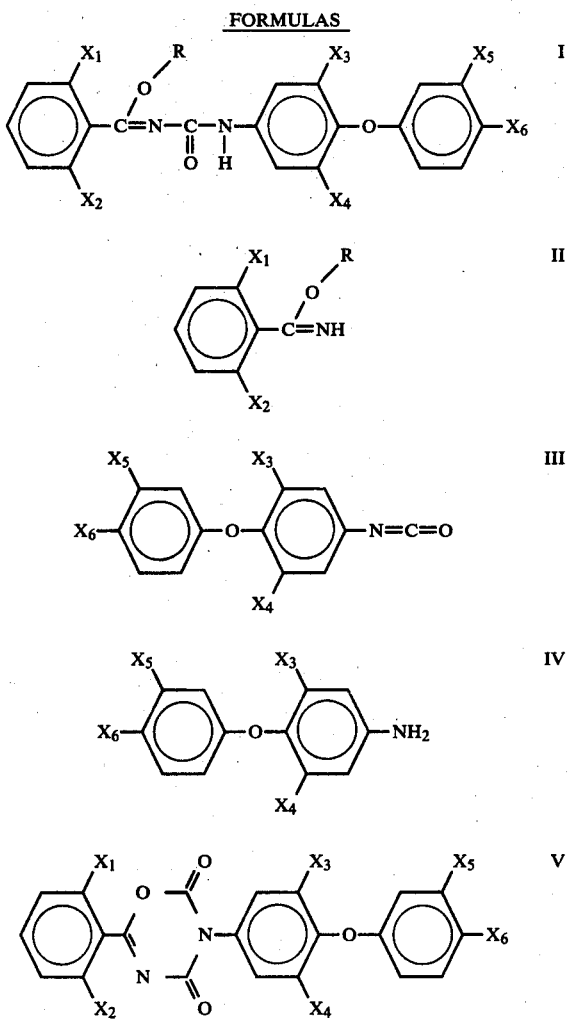

FORMULAS

I claim:
1. A compound of the formula:

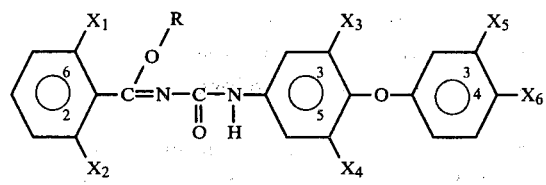

wherein $X_1$ is selected from the group consisting of methyl, trifloromethyl, chlorine, fluorine and bromine; $X_2$ is selected from the group consisting of hydrogen, methyl, trifluoromethyl, chlorine, fluorine and bromine; R is alkyl of from 1 to 5 carbon atoms; $X_3$ and $X_4$ can be the same or different and are selected from the group consisting of hydrogen, chlorine and bromine; $X_5$ is selected from the group consisting of hydrogen, chlorine, bromine and trifluoromethyl; and $X_6$ is selected from the group consisting of cyano and nitro; with the proviso that when $X_1$ and $X_2$ are chlorine or when $X_1$ is fluorine and $X_2$ is hydrogen then R, $X_3$, $X_4$, $X_5$ and $X_6$ are respectively not 1-methylethyl, chlorine, hydrogen, chlorine and nitro; with the further proviso that when $X_1$ is fluorine and $X_2$ is hydrogen then R, $X_3$, $X_4$, $X_5$ and $X_6$ are respectively not 1-methylethyl, chlorine, hydrogen, hyrogen and nitro; and with the further proviso that when $X_1$ is fluorine or methyl and $X_2$ is hydrogen then R, $X_3$, $X_4$, $X_5$ and $X_6$ are respectively not ethyl, hydrogen, hydrogen, hydrogen and nitro; and with the proviso that when $X_1$ and $X_2$ are florine, then R, $X_3$, $X_4$, $X_5$ and $X_6$ are respectively not ethyl, chlorine, hydrogen, chlorine and nitro.

2. A compound according to claim 1 wherein $X_1$ is selected from the group consisting of methyl, chlorine, fluorine and bromine; $X_2$ is hydrogen; $X_3$, $X_4$ and $X_5$ are chlorine and $X_6$ is selected from the group consisting of cyano and nitro.

3. A compound according to claim 1 wherein $X_1$ is trifluoromethyl; $X_2$ is hydrogen; R is selected from the group consisting of methyl, ethyl, propyl and isopropyl; $X_3$, $X_4$ and $X_5$ are chlorine and $X_6$ is selected from the group consisting of cyano and nitro.

4. A compound according to claim 1 wherein $X_1$ is selected from the group consisting of chlorine and fluorine; $X_2$ is hydrogen; $X_3$, $X_4$ and $X_5$ are chlorine; R is selected from the group consisting of methyl, ethyl, propyl and isopropyl; and $X_6$ is nitro.

5. A compound according to claim 1 wherein $X_1$ and $X_2$ are the same and are selected from the group consisting of fluorine and chlorine; R is selected from the group consisting of methyl, ethyl, propyl and isopropyl; $X_3$ and $X_4$ are chlorine; $X_5$ is hydrogen and $X_6$ is nitro.

6. A compound according to claim 1 wherein $X_1$ and $X_2$ are the same and are selected from the group consisting of fluorine and chlorine; R is selected from the group consisting of methyl, ethyl, propyl, and isopropyl; $X_3$ and $X_4$ are chlorine; $X_5$ is hydrogen and $X_6$ is nitro.

7. A compound according to claim 1 wherein $X_1$ is methyl; $X_2$ and $X_5$ are hydrogen; $X_3$ and $X_4$ are chlorine; $X_6$ is nitro.

8. A compound according to claim 1 wherein $X_1$, $X_3$ and $X_4$ are chlorine, $X_2$ and $X_5$ are hydrogen, $X_6$ is nitro and R is ethyl so that the specific embodiment is ethyl 2-chloro-N-[[[3,5-dichloro-4-(4-nitrophenoxy)phenyl]amino]carbonyl]benzenecarboximidate.

9. A compound according to claim 1 wherein $X_1$ is fluorine, $X_2$ and $X_5$ are hydrogen, $X_3$ and $X_4$ are chlorine, $X_6$ is nitro and R is ethyl so that the specific embodiment is ethyl N-[[[3,5-dichloro-4-(4-nitrophenoxy)phenyl]amino]carbonyl]-2-fluorobenzenecarboximidate.

10. A compound according to claim 1 wherein $X_1$, $X_2$, $X_3$ and $X_4$ are chlorine, $X_5$ is hydrogen, $X_6$ is nitro and R is ethyl so that the specific embodiment is ethyl 2,6-dichloro-N-[[[3,5-dichloro-4-(4-nitrophenoxy)phenyl]amino]carbonyl]benzenecarboximidate.

11. A compound according to claim 1 wherein $X_1$ and $X_2$ are fluorine, $X_3$ and $X_4$ are chlorine, $X_5$ is hydrogen, $X_6$ is nitro and R is ethyl so that the specific embodiment is ethyl N-[[[3,5-dichloro-4-(4-nitrophenoxy)phenyl]amino]carbonyl]-2,6-difluorobenzenecarboximidate.

12. A compound according to claim 1 wherein $X_1$ and $X_2$ are fluorine, $X_3$ is chlorine, $X_4$ and $X_5$ are hydrogen, $X_6$ is nitro and R is ethyl so that the specific embodiment is ethyl N-[[[3-chloro-4-(4-nitrophenoxy)phenyl]amino]carbonyl]-2,6-difluorobenzenecarboximidate.

13. A compound according to claim 1 wherein $X_1$ is methyl, $X_2$ and $X_5$ are hydrogen, $X_3$ and $X_4$ are chlorine, $X_6$ is nitro and R is ethyl so that the specific embodiment is ethyl N-[[[3,5-dichloro-4-(-4-nitrophenoxy)phenyl]amino]carbonyl]-2-methylbenzenecarboximidate.

14. A compound according to claim 1 wherein $X_3$, $X_4$ and $X_5$ are chlorine, $X_1$ is fluorine, $X_2$ is hydrogen, $X_6$ is nitro and R is ethyl so that the specific embodiment is ethyl N-[[[3,5-dichloro-4-(3-chloro-4-nitrophenoxy)phenyl]amino]carbonyl]-2-fluorobenzenecarboximidate.

15. A compound according to claim 1 wherein $X_2$, $X_4$ and $X_5$ are hydrogen, $X_1$ and $X_3$ are chlorine, $X_6$ is nitro and R is ethyl so that the specific embodiment is ethyl 2-chloro-N-[[[3-chloro-4-(4-nitrophenoxy)phenyl]amino]carbonyl]benzenecarboximidate.

16. A compound according to claim 1 wherein $X_1$ and $X_2$ are fluorine, $X_3$ and $X_4$ and $X_5$ are chlorine, $X_6$ is nitro and R is ethyl so that the specific embodiment is ethyl N-[[[3,5-dichloro-4-(3-chloro-4-nitrophenoxy)phenyl]amino]carbonyl]-2,6-difluorobenzenecarboximidate.

17. A compound according to claim 1 wherein $X_1$, $X_2$, $X_3$, $X_4$ and $X_5$ are chlorine, $X_6$ is nitro and R is ethyl so that the specific embodiment is ethyl 2,6-dichloro-N-[[[3,5-dichloro-4-(3-chloro-4-nitrophenoxy)phenyl]amino]carbonyl]benzenecarboximidate.

18. A compound according to claim 1 wherein $X_1$, $X_3$, $X_4$ and $X_5$ are chlorine, $X_2$ is hydrogen, $X_6$ is nitro and R is ethyl so that the specific embodiment is ethyl 2-chloro-N-[[[3,5-dichloro-4-(3-chloro-4-nitrophenoxy)phenyl]amino]carbonyl]benzenecarboximidate.

19. A compound according to claim 1 wherein $X_1$, $X_2$ and $X_3$ are chlorine, $X_4$ and $X_5$ are hydrogen, $X_6$ is nitro and R is ethyl so that the specific embodiment is ethyl 2,6-dichloro-N-[[[3-chloro-4-(4-nitrophenoxy)phenyl]amino]carbonyl]benzenecarboximidate.

20. A compound according to claim 1 wherein $X_2$, $X_4$ and $X_5$ are hydrogen, $X_1$ is fluorine, $X_3$ is chlorine, $X_6$ is nitro and R is ethyl so that the specific embodiment is ethyl N-[[[3-chloro-4-(4-nitrophenoxy)phenyl]amino]carbonyl]-2-fluorobenzenecarboximidate.

21. A compound according to claim 1 wherein $X_2$, $X_4$ and $X_5$ are hydrogen, $X_1$ and $X_3$ are chlorine, $X_6$ is nitro and R is isopropyl so that the specific embodiment is 1-methylethyl 2-chloro-N-[[[3-chloro-4-(4-nitrophenoxy)phenyl]amino]carbonyl]benzenecarboximidate.

22. A compound according to claim 1 wherein $X_1$, $X_2$ and $X_3$ are chlorine, $X_4$ and $X_5$ are hydrogen, $X_6$ is nitro and R is isopropyl so that the specific embodiment is 1-methylethyl N-[[[3-chloro-4-(4-nitrophenoxy)-phenyl]amino]carbonyl]-2,6-dichlorobenzenecarboximidate.

23. A compound according to claim 1 wherein $X_3$, $X_4$ and $X_5$ are chlorine, $X_1$ and $X_2$ are fluorine, $X_6$ is cyano and R is ethyl so that the specific embodiment is ethyl 2,6-difluoro-N-[[[3,5-dichloro-4-(3-chloro-4-cyanophenoxy)phenyl]amino]carbonyl]benzenecarboximidate.

24. A compound according to claim 1 wherein $X_1$, $X_2$, $X_3$, $X_4$ and $X_5$ are chlorine, $X_6$ is cyano and R is ethyl so that the specific embodiment is ethyl 2,6-dichloro-N-[[[3,5-dichloro-4-(3-chloro-4-cyanophenoxy)phenyl]amino]carbonyl]benzenecarboximidate.

25. A compound according to claim 1 wherein $X_1$, $X_3$, $X_4$ and $X_5$ are chlorine, $X_2$ is hydrogen, $X_6$ is cyano and R is ethyl so that the specific embodiment is ethyl 2-chloro-N-[[[3,5-dichloro-4-(3-chloro-4-cyanophenoxy)phenyl]amino]carbonyl]benzenecarboximidate.

26. A compound according to claim 1 wherein $X_1$ is methyl, $X_2$ and $X_4$ and $X_5$ are hydrogen, $X_3$ is chlorine, $X_6$ is nitro and R is ethyl so that the specific embodiment is ethyl N-[[[3-chloro-4-(4-nitrophenoxy)phenyl]amino]carbonyl]-2-methylbenzenecarboximidate.

27. A compound according to claim 1 wherein $X_1$ and $X_2$ are chlorine, $X_3$, $X_4$ and $X_5$ are hydrogen, $X_6$ is nitro and R is ethyl so that the specific embodiment is ethyl 2,6-dichloro-[[[4-(4-nitrophenoxy)phenyl]amino]carbonyl]-benzenecarboximidate.

28. A compound according to claim 1 wherein $X_1$ is selected from the group consisting of chlorine and fluorine, $X_1$ is hydrogen; $X_3$, $X_4$ and $X_5$ are chlorine; R is selected from the group consisting of methyl and ethyl; $X_6$ is nitro.

29. A compound according to claim 1 wherein $X_1$ and $X_2$ are the same and are selected from the group consisting of fluorine and chlorine; R is selected from the group consisting of methyl and ethyl; $X_3$ and $X_4$ are chlorine; $X_5$ is hydrogen and $X_6$ is nitro.

30. A compound according to claim 1 wherein $X_1$ and $X_2$ are the same and are selected from the group consisting of fluorine and chlorine; R is selected from the group consisting of methyl and ethyl; $X_3$ and $X_4$ are chlorine; $X_5$ is hydrogen and $X_6$ is nitro.

31. A compound selected from the group consisting of:
Ethyl 2-chloro-N-[[[3,5-dichloro-4-(4-nitrophenoxy)phenyl]amino]carbonyl]benzenecarboximidate,
Ethyl N-[[[3,5-dichloro-4-(4-nitrophenoxy)phenyl]amino]carbonyl]-2-fluorobenzenecarboximidate,
Ethyl 2,6-dichloro-N[[[3,5-dichloro-4-(4-nitrophenoxy)phenyl]amino]carbonyl]benzenecarboximidate,
Ethyl N-[[[3,5-dichloro-4-(4-nitrophenoxy)phenyl]amino]carbonyl]-2,6-difluorobenzenecarboximidate,
Ethyl N-[[[3-chloro-4-(4-nitrophenoxy)phenyl]amino]carbonyl]-2,6-difluorobenzenecarboximidate,
Ethyl N-[[[3,5-dichloro-4-(4-nitrophenoxy)phenyl]amino]carbonyl]-2-methylbenzenecarboximidate,
Ethyl N-[[[3,5-dichloro-4-(3-chloro-4-nitrophenoxy)phenyl]amino]carbonyl]-2-fluorobenzenecarboximidate,
Ethyl 2-chloro-N-[[[3-chloro-4-(4-nitrophenoxy)phenyl]amino]carbonyl]benzenecarboximidate,
1-Methylethyl 2-chloro-N-[[[3-chloro-4-(4-nitrophenoxy)phenyl]amino]carbonyl]benzenecarboximidate,
Ethyl N-[[[3,5-dichloro-4-(3-chloro-4-nitrophenoxy)phenyl]amino]carbonyl-2,6-difluorobenzenecarboximidate,
Ethyl 2,6-dichloro-N-[[[3,5-dichloro-4-(3-chloro-4-nitrophenoxy)phenyl]amino]carbonyl]benzenecarboximidate,
Ethyl 2-chloro-N-[[[3,5-dichloro-4-(3-chloro-4-nitrophenoxy)phenyl]amino]carbonyl]benzenecarboximidate,
Ethyl 2,6-dichloro-N-[[[3-chloro-4-(4-nitrophenoxy)phenyl]amino]carbonyl]benzenecarboximidate,
1-Methylethyl N-[[[3-chloro-4-(4-nitrophenoxy)phenyl]amino]carbonyl]-2,6-dichlorobenzenecarboximidate,
Ethyl N-[[[3-chloro-4-(4-nitrophenoxy)phenyl]amino]carbonyl]-2-fluorobenzenecarboximidate,
Ethyl 2,6-difluoro-N-[[[3,5-dichloro-4-(3-chloro-4-cyanophenoxy)phenyl]amino]carbonyl]benzenecarboximidate,
Ethyl 2,6-dichloro-N-[[[3,5-dichloro-4-(3-chloro-4-cyanophenoxy)phenyl]amino]carbonyl]benzenecarboximidate,
Ethyl 2-chloro-N-[[[3,5-dichloro-4-(3-chloro-4-cyanophenoxy)phenyl]amino]carbonyl]benzenecarboximidate,
Ethyl N-[[[3-chloro-4-(4-nitrophenoxy)phenyl]amino]carbonyl]-2-methylbenzenecarboximidate,
Ethyl 2-chloro-N-[[[3-chloro-4-(4-nitrophenoxy)phenyl]amino]carbonyl]benzenecarboximidate,
Ethyl N-[[[3-chloro-4-(3-chloro-4-nitrophenoxy)phenyl]amino]carbonyl]-2,6-dichlorobenzenecarboximidate,
Ethyl N-[[[3-chloro-4-(3-chloro-4-nitrophenoxy)phenyl]amino]carbonyl]-2-fluorobenzenecarboximidate,
Ethyl N-[[[3-chloro-4-(3-chloro-4-nitrophenoxy)phenyl]amino]carbonyl]-2-methylbenzenecarboximidate,
1-Methylethyl 2-chloro-N-[[[3-chloro-4-(3-chloro-4-nitrophenoxy)phenyl]amino]carbonyl]benzenecarboximidate,
Ethyl 2-chloro-N-[[[4-(4-nitrophenoxyl)phenyl]amino]carbonyl]benzenecarboximidate,
1-Methylethyl 2,6-dichloro-N-[[[3,5-dichloro-4-(3-chloro-4-cyanophenoxy)phenyl]amino]carbonyl]benzenecarboximidate,
Ethyl 2,6-dichloro-N-[[[4-(4-nitrophenoxy)phenyl]amino]carbonyl]benzenecarboximidate.

32. The method for controlling insect pests which comprises contacting susceptible insect pests with an effective amount of a compound of the formula:

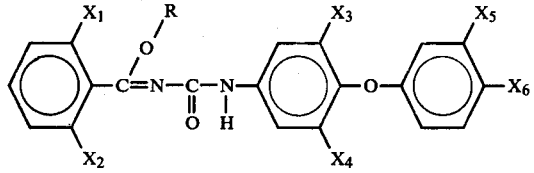

wherein $X_1$ is selected from the group consisting of methyl, trifloromethyl, chlorine, fluorine and bromine; $X_2$ is selected from the group consisting of hydrogen, methyl, trifluoromethyl, chlorine, fluorine and bromine; R is alkyl of from 1 to 5 carbon atoms; $X_3$ and $X_4$ can be the same or different and are selected from the group consisting of hydrogen, chlorine and bromine; $X_5$ is selected from the group consisting of hydrogen, chlorine, bromine and trifluoromethyl; and $X_6$ is selected from the group consisting of cyano and nitro; with the proviso that when $X_1$ and $X_2$ are chlorine or when $X_1$ is florine and $X_2$ is hydrogen then R, $X_3$, $X_4$, $X_5$ and $X_6$ are respectively not 1-methylethyl, chlorine, hydrogen, chlorine and nitro; with the further proviso that when $X_1$ is fluorine and $X_2$ is hydrogen then R, $X_3$, $X_4$, $X_5$ and $X_6$ are respectively not 1-methylethyl, chlorine, hydrogen, hydrogen and nitro; and with the further proviso that when $X_1$ is florine or methyl and $X_2$ is hydrogen then R, $X_3$, $X_4$, $X_5$ and $X_6$ are respectively not ethyl, hydrogen, hydrogen, hydrogen and nitro; and with the proviso that when $X_1$ and $X_2$ are florine, then R, $X_3$, $X_4$, $X_5$ and $X_6$ are respectively not ethyl, chlorine, hydrogen, chlorine and nitro.

33. The method according to claim 32 wherein $X_1$ is selected from the group consisting of methyl, chlorine, fluorine and bromine; $X_2$ is hydrogen; $X_3$, $X_4$ and $X_5$ are chlorine and $X_6$ is selected from the group consisting of cyano and nitro.

34. The method according to claim 32 wherein $X_1$ is trifluoromethyl; $X_2$ is hydrogen; R is selected from the group consisting of methyl, ethyl, propyl and isopropyl; $X_3$, $X_4$ and $X_5$ are chlorine and $X_6$ is selected from the group consisting of cyano and nitro.

35. The method according to claim 32 wherein $X_1$ is selected from the group consisting of chlorine and fluorine; $X_2$ is hydrogen; $X_3$, $X_4$ and $X_5$ are chlorine; R is selected from the group consisting of methyl, ethyl, propyl and isopropyl; and $X_6$ is nitro.

36. The method according to claim 32 wherein $X_1$ and $X_2$ are the same and are selected from the group consisting of fluorine and chlorine; R is selected from the group consisting of methyl, ethyl, propyl and isopropyl; $X_3$ and $X_4$ are chlorine; $X_5$ is hydrogen and $X_6$ is nitro.

37. The method according to claim 32 wherein $X_1$ and $X_2$ are the same and are selected from the group consisting of fluorine and chlorine; R is selected from the group consisting of methyl, ethyl, propyl, and isopropyl; $X_3$ and $X_4$ are chlorine; $X_5$ is hydrogen and $X_6$ is nitro.

38. The method according to claim 32 wherein $X_1$ is methyl; $X_2$ and $X_5$ are hydrogen; $X_3$ and $X_4$ are chlorine; $X_6$ is nitro.

39. The method according to claim 32 wherein the active ingredient is selected from the group consisting of:

Ethyl 2-chloro-N-[[[3,5-dichloro-4-(4-nitrophenoxy)phenyl]amino]carbonyl]benzenecarboximidate,
Ethyl N-[[[3,5-dichloro-4-(4-nitrophenoxy)phenyl]amino]carbonyl]-2-fluorobenzenecarboximidate,
Ethyl -2,6-dichloro-N-[[[3,5-dichloro-4-(4-nitrophenoxy)phenyl]amino]carbonyl]benzenecarboximidate,
Ethyl N-[[[3,5-dichloro-4-(4-nitrophenoxy)phenyl]amino]carbonyl]-2,6-difluorobenzenecarboximidate,
Ethyl N-[[[3-chloro-4-(4-nitrophenoxy)phenyl]amino]carbonyl]2,6-difluorobenzenecarboximidate,
Ethyl N-[[[3,5-dichloro-4-(4-nitrophenoxy)phenyl]amino]carbonyl]2-methylbenzenecarboximidate,
Ethyl N-[[[3,5-dichloro-4-(3-chloro-4-nitrophenoxy)phenyl]amino]carbonyl]-2-fluorobenzenecarboximidate,
Ethyl 2-chloro-N-[[[3-chloro-4-(4-nitrophenoxy)phenyl]amino]carbonyl]benzenecarboximidate,
1-Methylethyl 2-chloro-N-[[[3-chloro-4-(4-nitrophenoxy)phenyl]amino]carbonyl]benzenecarboximidate,
Ethyl N-[[[3,5-dichloro-4-(3-chloro-4-nitrophenoxy)phenyl]amino]carbonyl]2,6-difluorobenzenecarboximidate,
Ethyl 2,6-dichloro-N-[[[3,5-dichloro-4-(3-chloro-4-nitrophenoxy)phenyl]amino]carbonyl]benzenecarboximidate,
Ethyl 2-chloro-N-[[[3,5-dichloro-4-(3-chloro-4-nitrophenoxy)phenyl]amino]carbonyl]benzenecarboximidate,
Ethyl 2,6-dichloro-N-[[[3-chloro-4-(4-nitrophenoxy)phenyl]amino]carbonyl]benzenecarboximidate,
1-Methylethyl N-[[[3-chloro-4-(4-nitrophenoxy)phenyl]amino]carbonyl]-2,6-dichlorobenzenecarboximidate,
Ethyl N-[[[3-chloro-4-(4-nitrophenoxy)phenyl]amino]carbonyl]-2-fluorobenzenecarboximidate,
Ethyl 2,6-difluoro-N-[[[3,5-dichloro-4-(3-chloro-4-cyanophenoxy)phenyl]amino]carbonyl]benzenecarboximidate,
Ethyl 2,6-dichloro-N-[[[3,5-dichloro-4-(3-chloro-4-cyanophenoxy)phenyl]amino]carbonyl]benzenecarboximidate,
Ethyl 2-chloro-N-[[[3,5-dichloro-4-(3chloro-4-cyanophenoxy)phenyl]amino]carbonyl]benzenecarboximidate,
Ethyl N-[[[3-chloro-4-(4-nitrophenoxy)phenyl]amino]carbonyl]-2-methylbenzenecarboximidate,
Ethyl 2-chloro-N-[[[3-chloro-4-(3-chloro-4-nitrophenoxy)phenyl]amino]carbonyl]benzenecarboximidate,
Ethyl N-[[[3-chloro-4-(3-chloro-4-nitrophenoxy)phenyl]amino]carbonyl]-2,6-dichlorobenzenecarboximidate,
Ethyl N-[[[3-chloro-4-(3-chloro-4-nitrophenoxy)phenyl]amino]carbonyl]-2-fluorobenzenecarboximidate,
Ethyl N-[[[3-chloro-4-(3-chloro-4-nitrophenoxy)phenyl]amino]carbonyl]-2-methylbenzenecarboximidate,
Ethyl 2,6-dichloro-N-[[[4-(4-nitrophenoxy)phenyl]amino]carbonyl]benzenecarboximidate.

40. Formulations for pest control comprising an adjuvant carrier and as active ingredient a biologically effective amount of one or more compounds of the formula:

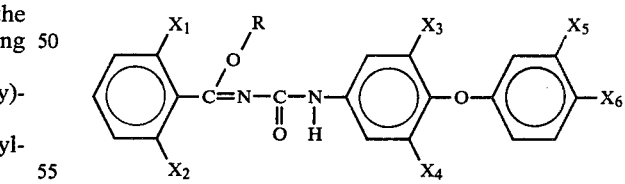

wherein $X_1$ is selected from the group consisting of methyl, trifluoromethyl, chlorine, fluorine and bromine; $X_2$ is selected from the group consisting of hydrogen, methyl, trifluoromethyl, chlorine, fluorine and bromine; R is alkyl of from 1 to 5 carbon atoms; $X_3$ and $X_4$ can be the same or different and are selected from the group consisting of hydrogen, chlorine and bromine; $X_5$ is selected from the group consisting of hydrogen, chlorine, bromine and trifluoromethyl; and $X_6$ is selected from the group consisting of cyano and nitro; with the proviso that when $X_1$ and $X_2$ are chlorine or when $X_1$ is fluorine and $X_2$ is hydrogen then R, $X_3$, $X_4$, $X_5$ and $X_6$ are respectively not 1-methylethyl, chlorine, hydrogen, chlorine and nitro; with the further proviso that when $X_1$ is fluorine and $X_2$ is hydrogen then R, $X_3$, $X_4$, $X_5$ and $X_6$ are respectively not 1-methylethyl, chlorine, hydrogen, hydrogen and nitro; and with the further proviso that when $X_1$ is florine or methyl and $X_2$ is hydrogen then R, $X_3$, $X_4$, $X_5$ and $X_6$ are respectively not ethyl, hydrogen, hydrogen, hydrogen and nitro; and with the proviso that when $X_1$ and $X_2$ are florine, then R, $X_3$, $X_4$, $X_5$ and $X_6$ are respectively not ethyl, chlorine, hydrogen, chlorine and nitro.

41. Formulations according to claim 40 wherein the active ingredient compounds consist of compounds selected from the group consisting of:

Ethyl 2-chloro-N-[[[3,5-dichloro-4-(4-nitrophenoxy)phenyl]amino]carbonyl]benzenecarboximidate,
Ethyl N-[[[3,5-dichloro-4-(4-nitrophenoxy)phenyl]amino]carbonyl]2-fluorobenzenecarboximidate,
Ethyl 2,6-dichloro-N-[[[3,5-dichloro-4-(4-nitrophenoxy)phenyl]amino]carbonyl]benzenecarboximidate,
Ethyl N-[[[3,5-dichloro-4-(4-nitrophenoxy)phenyl]amino]carbonyl]-2,6-difluorobenzenecarboximidate,
Ethyl N-[[[3-chloro-4-(4-nitrophenoxy)phenyl]amino]carbonyl]-2,6-difluorobenzenecarboximidate,
Ethyl N-[[[3,5-dichloro-4-(4-nitrophenoxy)phenyl]amino]carbonyl]-2-methylbenzenecarboximidate,
Ethyl N-[[[3,5-dichloro-4-(3-chloro-4-nitrophenoxy)phenyl]amino]carbonyl]-2-fluorobenzenecarboximidate,
Ethyl 2-chloro-N-[[[3-chloro-4-(4-nitrophenoxy)phenyl]amino]carbonyl]benzenecarboximidate,
1-Methylethyl 2-chloro-N-[[[3-chloro-4-(4-nitrophenoxy)phenyl]amino]carbonyl]benzenecarboximidate,
Ethyl N-[[[3,5-dichloro-4-(3-chloro-4-nitrophenoxy)phenyl]amino]carbonyl]-2,6-difluorobenzenecarboximidate,
Ethyl 2,6-dichloro-N-[[[3,5-dichloro-4-(3-chloro-4-nitrophenoxy)phenyl]amino]carbonyl]benzenecarboximidate,
Ethyl 2-chloro-N-[[[3,5-dichloro-4-(3-chloro-4-nitrophenoxy)phenyl]amino]carbonyl]benzenecarboximidate,
Ethyl 2,6-dichloro-N-[[[3-chloro-4-(4-nitrophenoxy)phenyl]amino]carbonyl]benzenecarboximidate,
1-Methylethyl N-[[[3-chloro-4-(4-nitrophenoxy)phenyl]amino]carbonyl]-2,6-dichlorobenzenecarboximidate,
Ethyl N-[[[3-chloro-4-(4-nitrophenoxy)phenyl]amino]carbonyl]-2-fluorobenzenecarboximidate,
Ethyl 2,6-difluoro-N-[[[3,5-dichloro-4-(3-chloro-4-cyanophenoxy)phenyl]amino]carbonyl]benzenecarboximidate,
Ethyl 2,6-dichloro-N-[[[3,5-dichloro-4-(3-chloro-4-cyanophenoxy)phenyl]amino]carbonyl]benzenecarboximidate,
Ethyl 2-chloro-N-[[[3,5-dichloro-4-(3-chloro-4-cyanophenoxy)phenyl]amino]carbonyl]benzenecarboximidate,
Ethyl N-[[[3-chloro-4-(4-nitrophenoxy)phenyl]amino]carbonyl]-2-methylbenzenecarboximidate,
Ethyl 2-chloro-N-[[[3-chloro-4-(3-chloro-4-nitrophenoxy)phenyl]amino]carbonyl]benzenecarboximidate,
Ethyl N-[[[3-chloro-4-(3-chloro-4-nitrophenoxy)phenyl]amino]carbonyl]-2,6-dichlorobenzenecarboximidate,
Ethyl N-[[[3-chloro-4-(3-chloro-4-nitrophenoxy)phenyl]amino]carbonyl]-2-fluorobenzenecarboximidate,
Ethyl N-[[[3-chloro-4-(3-chloro-4-nitrophenoxy)phenyl]amino]carbonyl]-2-methylbenzenecarboximidate,
Ethyl 2,6-dichloro-N-[[[4-(nitrophenoxy)phenyl]amino]carbonyl]benzenecarboximidate.

42. A compound selected from the group consisting of:

Methyl 2-chloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]-2-fluorobenzenecarboximidate,
Methyl 2,6-dichloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]-2,6-difluorobenzenecarboximidate,
Methyl N-[[[3-chloro-4-(4-nitrophenoxy)phenyl]amino]carbonyl]-2,6-difluorobenzenecarboximidate,
Methyl N-[[[3,5-dichloro-4-(4-nitrophenoxy)phenyl]amino]carbonyl]-2-methylbenzenecarboximidate,
Methyl 2-chloro-N-[[[3-chloro-4-(4-nitrophenoxy)phenyl]amino]carbonyl]benzenecarboximidate,
Methyl N-[[[3-chloro-4-(4-nitrophenoxy)phenyl]amino]carbonyl]-2,6-dichlorobenzenecarboximidate,
Methyl N-[[[3-chloro-4-(4-nitrophenoxy)phenyl]amino]carbonyl]-2-fluorobenzenecarboximidate,
Methyl N-[[[3-chloro-4-(4-nitrophenoxy)phenyl]amino]carbonyl]-2-methylbenzenecarboximidate,
1-Methylethyl 2-chloro-N-[[[3,5-dichloro-4-(4-nitrophenoxy)phenyl]amino]carbonyl]benzenecarboximidate,
1-Methylethyl N-[[[3,5-dichloro-4-(4-nitrophenoxy)phenyl]amino]carbonyl]-2-fluorobenzenecarboximidate,
1-Methylethyl 2,6-dichloro-N-[[[3,5-dichloro-4-(4-nitrophenoxy)phenyl]amino]carbonyl]benzenecarboximidate,
1-Methylethyl N-[[[3,5-dichloro-4-(4-nitrophenoxy)phenyl]amino]carbonyl]-2,6-difluorobenzenecarboximidate,
1-Methylethyl N-[[[3-chloro-4-(4-nitrophenoxy)phenyl]amino]carbonyl]-2,6-difluorobenzenecarboximidate,
1-Methylethyl N-[[[3,5-dichloro-4-(4-nitrophenoxy)phenyl]amino]carbonyl]-2-methylbenzenecarboximidate,
1-Methylethyl N-[[[3-chloro-4-(4-nitrophenoxy)phenyl]amino]carbonyl]-2-fluorobenzenecarboximidate,
1-Methylethyl N-[[[3-chloro-4-(4-nitrophenoxy)phenyl]amino]carbonyl]-2-methylbenzenecarboximidate.

43. The method according to claim 32 wherein the active ingredient is selected from the group consisting of:

Methyl 2-chloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]-2-fluorobenzenecarboximidate,
Methyl 2,6-dichloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]-2,6-difluorobenzenecarboximidate,
Methyl N-[[[3-chloro-4-(4-nitrophenoxy)phenyl]amino]carbonyl]2,6-difluorobenzenecarboximidate,
Methyl N-[[[3,5-dichloro-4-(4-nitrophenoxy)phenyl]amino]carbonyl]-2-methylbenzenecarboximidate, Methyl 2-chloro-N-[[[3-chloro-4-(4-nitrophenoxy)phenyl]amino]carbonyl]benzenecarboximidate,
Methyl N-[[[3-chloro-4-(4-nitrophenoxy)phenyl]amino]carbonyl]-2,6-dichlorobenzenecarboximidate,
Methyl N-[[[3-chloro-4-(4-nitrophenoxy)phenyl]amino]carbonyl]-2-fluorobenzenecarboximidate,
Methyl N-[[[3-chloro-4-(4-nitrophenoxy)phenyl]amino]carbonyl]-2-methylbenzenecarboximidate,
1-Methylethyl 2-chloro-N-[[[3,5-dichloro-4-(4-nitrophenoxy)phenyl]-amino]carbonyl]benzenecarboximidate,
1-Methylethyl N-[[[3,5-dichloro-4-(4-nitrophenoxy)phenyl]amino]carbonyl]-2-fluorobenzenecarboximidate,
1-Methylethyl 2,6-dichloro-N-[[[3,5-dichloro-4-(4-nitrophenoxy)phenyl]-amino]carbonyl]benzenecarboximidate,
1-Methylethyl N-[[[3,5-dichloro-4-(4-nitrophenoxy)phenyl]amino]carbonyl]-2,6-difluorobenzenecarboximidate,
1-Methylethyl N-[[[3-chloro-4-(4-nitrophenoxy)phenyl]amino]carbonyl]-2,6-difluorobenzenecarboximidate,
1-Methylethyl N-[[[3,5-dichloro-4-(4-nitrophenoxy)phenyl]amino]carbonyl]-2-methylbenzenecarboximidate,
1-Methylethyl N-[[[3-chloro-4-(4-nitrophenoxy)phenyl]amino]carbonyl]-2-fluorobenzenecarboximidate,
1-Methylethyl N-[[[3-chloro-4-(4-nitrophenoxy)phenyl]amino]carbonyl]-2-methylbenzenecarboximidate.

44. Formulations according to claim 40 wherein the active ingredient compounds consist of compounds selected from the group consisting of:
Methyl 2-chloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]-2-fluorobenzenecarboximidate,
Methyl 2,6-dichloro-N-[[[3,5-dichloro-4-(4-nitrophenoxy)phenyl]amino]carbonyl]benzenecarboximidate,
Methyl N-[[[3,5-dichloro-4-(4-nitrophenoxy)phenyl]amino]carbonyl]-2,6-difluorobenzenecarboximidate,
Methyl N-[[[3-chloro-4-(4-nitrophenoxy)phenyl]amino]carbonyl]2,6-difluorobenzenecarboximidate,
Methyl N-[[[3,5-dichloro-4-(4-nitrophenoxy)phenyl]amino]carbonyl]-2-methylbenzenecarboximidate,
Methyl 2-chloro-N-[[[3-chloro-4-(4-nitrophenoxy)phenyl]amino]carbonyl]benzenecarboximidate,
Methyl N-[[[3-chloro-4-(4-nitrophenoxy)phenyl]amino]carbonyl]-2,6-dichlorobenzenecarboximidate,
Methyl N-[[[3-chloro-4-(4-nitrophenoxy)phenyl]amino]carbonyl]-2-fluorobenzenecarboximidate,
Methyl N-[[[3-chloro-4-(4-nitrophenoxy)phenyl]amino]carbonyl]-2-methylbenzenecarboximidate,
1-Methylethyl 2-chloro-N-[[[3,5-dichloro-4-(4-nitrophenoxy)phenyl]amino]carbonyl]benzenecarboximidate,
1-Methylethyl N-[[[3,5-dichloro-4-(4-nitrophenoxy)phenyl]amino]carbonyl]-2-fluorobenzenecarboximidate,
1-Methylethyl 2,6-dichloro-N-[[[3,5-dichloro-4-(4-nitrophenoxy)phenyl]amino]carbonyl]benzenecarboximidate,
1-Methylethyl N-[[[3,5-dichloro-4-(4-nitrophenoxy)phenyl]amino]carbonyl]-2,6-difluorobenzenecarboximidate,
1-Methylethyl N-[[[3-chloro-4-(4-nitrophenoxy)phenyl]amino]carbonyl]-2,6-difluorobenzenecarboximidate,
1-Methylethyl N-[[[3,5-dichloro-4-(4-nitrophenoxy)phenyl]amino]carbonyl]2-methylbenzenecarboximidate,
1-Methylethyl N-[[[3-chloro-4-(4-nitrophenoxy)phenyl]amino]carbonyl]-2-fluorobenzenecarboximidate,
1-Methylethyl N-[[[3-chloro-4-(4-nitrophenoxy)phenyl]amino]carbonyl]-2-methylbenzenecarboximidate.

* * * * *

UNITED STATES PATENT OFFICE
CERTIFICATE OF CORRECTION

Patent No. 4,357,347                    Dated  November 2, 1982

Inventor(s)  Stephen J. Nelson

It is certified that error appears in the above-identified patent and that said Letters Patent are hereby corrected as shown below:

Column 6, line 60:  "c," should read:  --C,--.
Column 18, line 65: "trifloromethyl" should read:  --trifluoromethyl--.

Signed and Sealed this

Second Day of October 1984

[SEAL]

Attest:

GERALD J. MOSSINGHOFF

Attesting Officer          Commissioner of Patents and Trademarks